United States Patent [19]

Pieper

[11] Patent Number: Plant 5,872

[45] Date of Patent: Feb. 3, 1987

[54] *AECHMEA FASCINI* FRIEDERIKE

[76] Inventor: Wilhelm Pieper, Dehmke, auf der Horst 2, 3258 Aerzen 9, Fed. Rep. of Germany

[21] Appl. No.: 668,874

[22] Filed: Nov. 6, 1984

[51] Int. Cl.[4] ..... A01H 5/00

[52] U.S. Cl. ..... Plt./88

[58] Field of Search ..... Plt./88

[56] References Cited

U.S. PATENT DOCUMENTS

P.P. 898 11/1949 Foster .

FOREIGN PATENT DOCUMENTS

B124P 2/1983 Fed. Rep. of Germany .

B124P 1/1983 Netherlands .

OTHER PUBLICATIONS

Reprint from Gartenbau-Wissenschaft (Horticultural Science) 5/6/84, vol. 39(21), pp. 569–574.

Reprint from Die Orchidee (The Orchid), #28, 1977, pp. 118–122.

Further Investigations into the Cultivation of Aechmea in vitro, K. Zimmer and W. Pieper, Mar. 1975, pp. 129–132.

Reprint from Gartenwelt (Garden World), vol. 76, No. 5 of 6, Mar. 1976, pp. 93–95.

*Primary Examiner*—Robert E. Bagwill

*Attorney, Agent, or Firm*—Russell, Georges, Breneman, Hellwege & Yee

[57] ABSTRACT

A new variety of *Aechmea fascini* is disclosed which is characterized by the absence of spines along the margins of the leaves of the plant.

5 Drawing Figures

DESCRIPTION

The present invention relates to a new and distinct variety of *Aechmea fascini.*

This new cultivation was developed by me in my laboratory at Aerzen, Federal Republic of Germany, through controlled breeding by means of the introduction of mutagenes into cultures of suspensions of cells of *Aechmea fascini* (*Aechmea fascini* being the result of the cross-breeding of *Aechmea chantinii* ♀ and *Aechmea fasciata*). Repeated asexual reproduction by means of meristematic cultures has shown that the unique features of this new variety of *Aechmea fascini* (designated *Aechmea fascini* Friederike) are stabilized and are reproduced true to type in subsequent propagations. No tendency has been observed for the characteristics of the new variety to revert to those of its parent.

This new variety of plant may be compared with *Aechmea fascini,* with the most striking comparison being that the new variety has leaves whose margins are smooth while the leaves of the *Aechmea fascini* include black spines along the margins which spines are approximately 4 mm. in length and spaced about 10 mm. apart. The absence of the spines is highly advantageous as it greatly facilitates handling of the plant. The new variety otherwise retains the basic characteristics of the *Aechmea fascini.* The plant is sterile and can be bred only vegetatively and is also resistant to fusarium disease.

The accompanying drawings clearly depict the new variety while providing a comparison to the *Aechmea fascini.*

Figure 1:
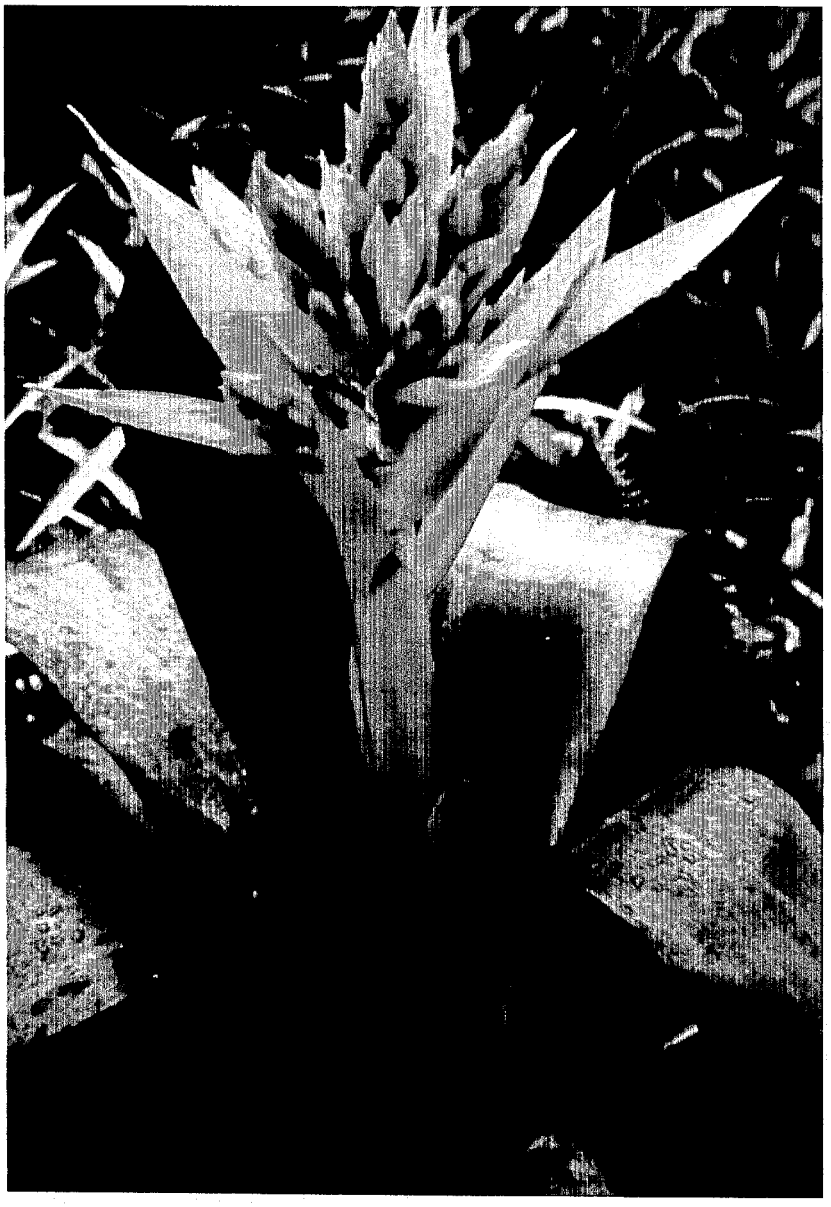
FIGS. 1 and 2 are photographs of the *Aechmea fascini* Friederike cultivar of the present invention.
Figure 2:
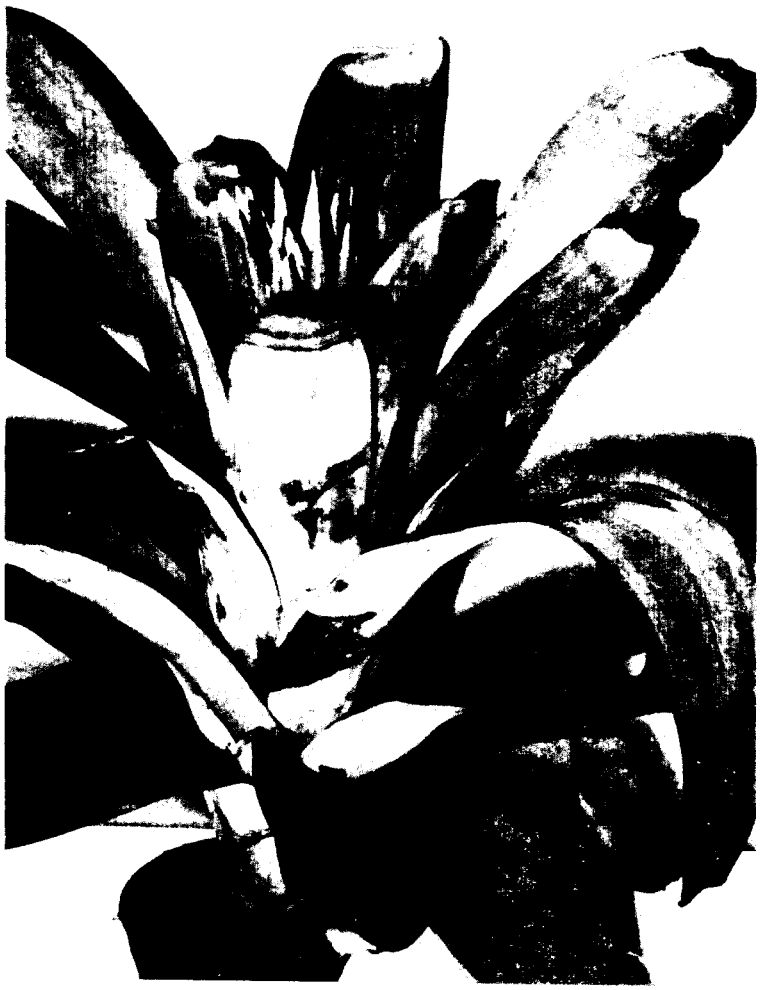
Figure 3:
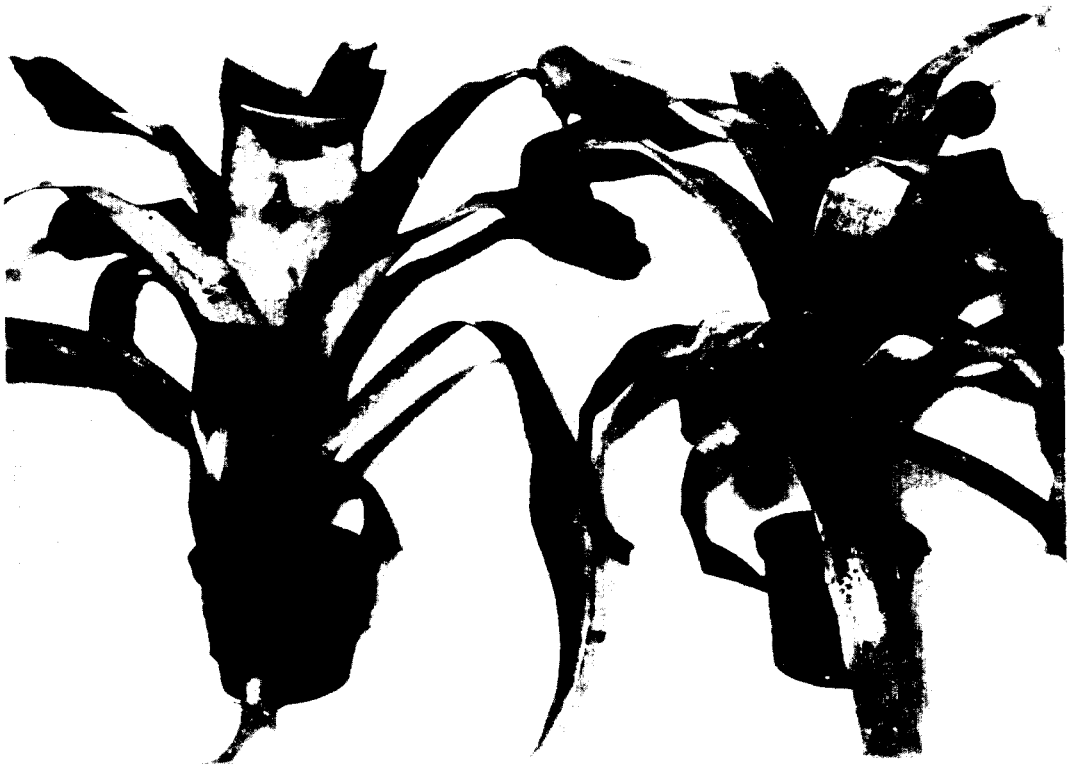
FIG. 3 is a photograph of the *Aechmea fascini* Friederike cultivar of the present invention (right hand portion of photograph) and of the *Aechmea fascini* (left hand portion of photograph) in a side-by-side relationship, with the respective plants being of substantially the same age and having been cultivated under similar conditions.
Figure 4:
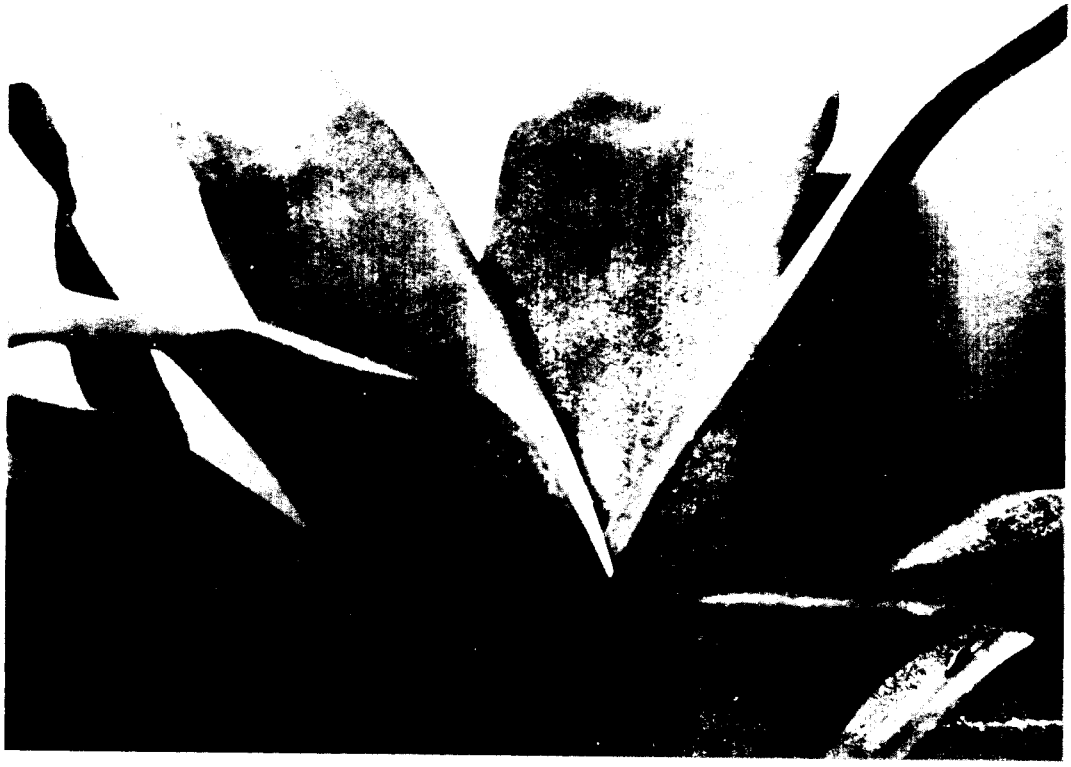
FIG. 4 is a photograph of the smooth, spine-less margins of the leaves of the *Aechmea fascini* Friederike cultivar of the present invention.
Figure 5:
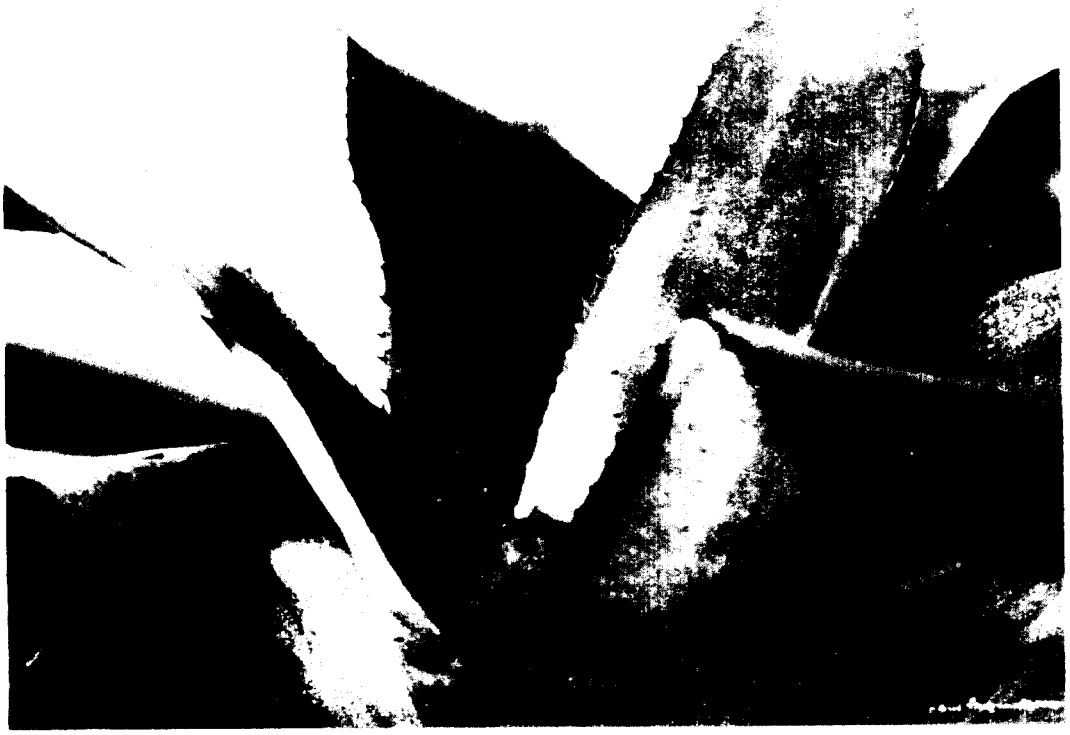
PRIOR ART FIG. 5
FIG. 5 is a photograph of the spine-containing margins of the leaves of *Aechmea fascini.*

As the photographs indicate, the characteristics of the *Aechmea fascini* Friederike closely correspond to the characteristics of the *Aechmea fascini.* Importantly, the FIGS. 4 and 5 demonstrate that the smooth margins of the leaves of the new cultivar contrast dramatically with the spine-containing margins of the *Aechmea fascini.*

A further botanical description of the new variety follows:

Plant shape: stemless, reaching 70 to 80 cm. in height when blooming.

Foliage: numerous leaves, forming an upright-spreading funnel-shaped rosette with a height of up to 50 cm. and being up to 50 cm. in diameter.

Leaf Sheath: indistinctly set off against the scape, having a length of up to 9 cm. and a width of up to 8 cm., the upper sides nearly bare, pale green, pale violet in the middle, the undersides being densely covered with white scales.

Leaf Blade: wide and tongue-shaped (ligulated), up to 9 cm. wide and up to 35 cm. long, contracted in a very short, mostly backward bended tip, having smooth, spineless margins the upper side initially densely covered with grey scales, the bottom side being covered with silvery white scales.

Scape: upright, longer than the rosette leaves, about 50 cm. long and 1 cm. thick, round, reddish green, with dense white woolen hair clinging to the scape.

Scape bracts: upright, clinging to the scape, longish-lanciformly pointed, the central bracts being up to 12 cm. long and 2 cm. wide, both sides scatteredly lepidote, mostly having spines in the margins towards the tip, shiny carmine.

Inflorescence: loosely bipinnate, 15 cm. long, generally 10 cm. wide, having generally uprightly spread-out spikes.

Primary bracts: similar to the upper scape bracts, mostly longer than the spikes.

Spikes: roundish, having a length of up to 10 cm. and a width of up to 2 cm., pointed, having a short, flattened, white-fluffy peduncle with a length of 1 cm.

Flower Bracts: the basal ones are arranged in two rows, the central and upper ones being arranged scatteredly, being up to 2.5 cm. long (spread out) and 1.5 cm. wide, acutely pointed, carinate towards the tip, shiny vermilion at the upper half, greenish towards the base, at the bottom sides white lepidote, surpassing the sepals in height.

Sepals: up to 1.5 cm. long, up to 1 cm. wide, almost naked, indistinctly keeled, very short pointed.

Petals: 2 cm. in length, upright, blue on the tips, reddish towards the base, no ligula.

Stamens and Pistil: encased.

Ovary: 0.7 cm. high, 5 mm. thick.

I claim:

1. A new and distinct variety of *Aechmea fascini*, substantially as herein shown and described and characterized particularly as to novelty by the smooth margins of its leaves.

* * * * *

PRIOR ART NEW CULTIVAR